(12) United States Patent
Rao et al.

(10) Patent No.: US 11,896,395 B2
(45) Date of Patent: Feb. 13, 2024

(54) CATHETER WITH INSERT-MOLDED MICROELECTRODE

(71) Applicant: Biosense Webster (Israel) Ltd., Yokneam (IL)

(72) Inventors: Anand R. Rao, Tustin, CA (US); Keshava Datta, Chino Hills, CA (US); Thanh V. Nguyen, El Monte, CA (US); Thomas V. Selkee, Claremont, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 702 days.

(21) Appl. No.: 16/994,745

(22) Filed: Aug. 17, 2020

(65) Prior Publication Data

US 2021/0077027 A1 Mar. 18, 2021

Related U.S. Application Data

(60) Provisional application No. 62/901,285, filed on Sep. 17, 2019.

(51) Int. Cl.
*A61B 5/00* (2006.01)
*A61B 18/14* (2006.01)
(Continued)

(52) U.S. Cl.
CPC ........ *A61B 5/6852* (2013.01); *A61B 18/1492* (2013.01); *A61B 34/20* (2016.02); *A61B 2017/00199* (2013.01); *A61B 2017/00327* (2013.01); *A61B 2017/00526* (2013.01); *A61B 2018/00077* (2013.01); *A61B 2018/00351* (2013.01); *A61B 2018/00577* (2013.01); *A61B 2018/00613* (2013.01); *A61B 2018/00821* (2013.01); *A61B 2034/2048* (2016.02);
(Continued)

(58) Field of Classification Search
CPC .... A61B 5/287; A61B 5/6852; A61B 18/1492
See application file for complete search history.

(56) References Cited

U.S. PATENT DOCUMENTS

| 5,738,096 A | 4/1998 | Ben-Haim |
| 8,956,353 B2 | 2/2015 | Govari et al. |

(Continued)

FOREIGN PATENT DOCUMENTS

| EP | 2944282 A1 * | 11/2015 | ......... A61B 18/1492 |
| EP | 2944282 A1 | 11/2015 | |

OTHER PUBLICATIONS

International Search Report and Written Opinion dated Jan. 14, 2021, for International Application No. PCT/IB2020/058495, 9 pages.

*Primary Examiner* — Eun Hwa Kim
(74) *Attorney, Agent, or Firm* — Lewis Roca Rothgerber Christie LLP

(57) ABSTRACT

An apparatus includes a catheter assembly for use in a medical procedure to conduct electrophysiological mapping. The catheter assembly includes a catheter having an end effector with a tip member. One or more insert-molded microelectrodes are located in the tip member of the end effector for conducting electrophysiological mapping. The insert-molded microelectrodes include a microelectrode and a composite that isolates the microelectrode from contact with the tip member.

17 Claims, 10 Drawing Sheets

(51) Int. Cl.
  *A61B 34/20* (2016.01)
  *A61B 18/00* (2006.01)
  *A61B 17/00* (2006.01)

(52) U.S. Cl.
  CPC ........... *A61B 2034/2055* (2016.02); *A61B 2034/2063* (2016.02); *A61B 2218/002* (2013.01); *A61B 2562/028* (2013.01); *A61B 2562/0261* (2013.01); *A61B 2562/125* (2013.01)

(56) References Cited

U.S. PATENT DOCUMENTS

| | | |
|---|---|---|
| 9,480,416 B2 | 11/2016 | Govari et al. |
| 9,801,585 B2 | 10/2017 | Shah et al. |
| 9,907,480 B2 | 3/2018 | Basu et al. |
| 10,130,422 B2 | 11/2018 | Ditter |
| 11,738,200 B2 * | 8/2023 | Viswanathan .......... A61B 5/352 600/510 |
| 2008/0243214 A1 * | 10/2008 | Koblish ............. A61B 18/1492 606/41 |
| 2010/0331658 A1 * | 12/2010 | Kim ....................... A61B 18/18 29/428 |
| 2013/0030426 A1 | 1/2013 | Gallardo et al. |
| 2016/0128765 A1 | 5/2016 | Schultz et al. |
| 2016/0143690 A1 | 5/2016 | Schultz et al. |
| 2017/0312022 A1 | 11/2017 | Beeckler et al. |
| 2018/0056038 A1 | 3/2018 | Aujla |
| 2018/0071009 A1 * | 3/2018 | Bar-Tal ................. A61B 18/14 |
| 2018/0071017 A1 | 3/2018 | Bar-tal et al. |

\* cited by examiner

CATHETER WITH INSERT-MOLDED MICROELECTRODE

PRIORITY

This application claims priority to U.S. Provisional Pat. App. No. 62/901,285, entitled "Catheter with Insert-Molded Microelectrode," filed Sep. 17, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., alternating-current or direct-current energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with electrical energy to thereby ablate the contacted tissue. In some cases, the electrodes may be bipolar. In some other cases, a monopolar electrode may be used in conjunction with a ground pad or other reference electrode that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

When using an ablation catheter, it may be desirable to ensure that one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue. Another indirect method that could also employed is to monitor the impedance level on the microelectrodes or tip dome to determine amount of tissue contact.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Ablation Catheter System

Figure 1:
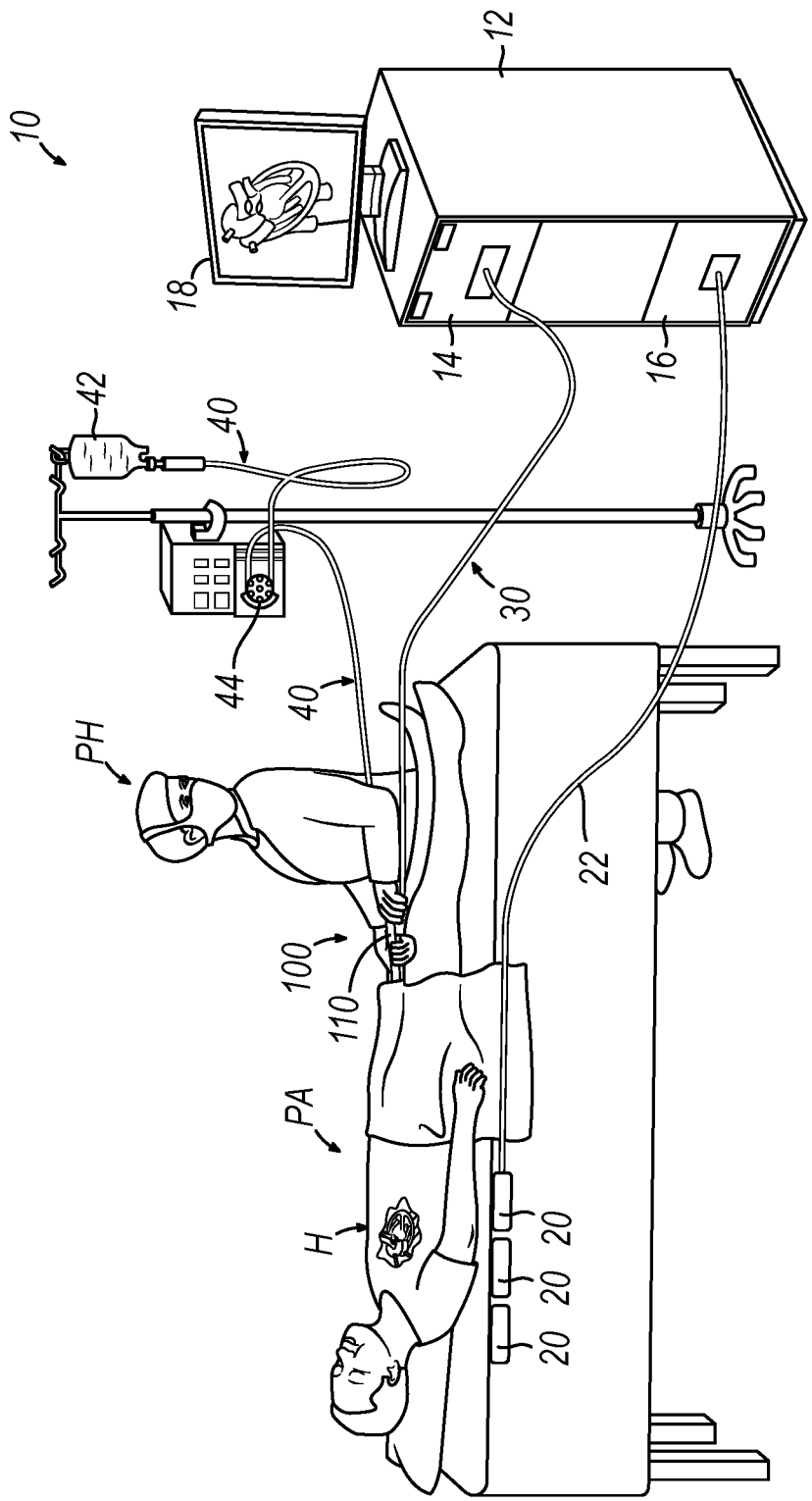
FIG. 1 depicts a schematic view of a medical procedure in which a catheter of a catheter assembly is inserted in a patient.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2 and 4 but not shown in FIG. 1) of catheter assembly (100) disposed in a patient (PA) to ablate tissue in or near the heart (H) of the patient (PA). Catheter assembly (100) includes handle (110), catheter (120) extending distally from handle (110), end effector (140) located at a distal end of catheter (120), and a user input feature (190) located on handle. As used herein, the term "ablate" is intended to cover either radio-frequency ablation or irreversible electroporation.

As will be described in greater detail below, end effector (140) includes various components configured to deliver electrical energy to targeted tissue sites, provide EP mapping functionality, track external forces imparted on end effector (140), track the location of end effector (140), and disperse irrigation fluid. As will also be described in greater detail below, user input feature (190) is configured to deflect end effector (140) and a distal portion of catheter (120) away from a central longitudinal axis (L-L) (FIGS. 3-4) defined by a proximal portion of catheter (120).

Figure 2:
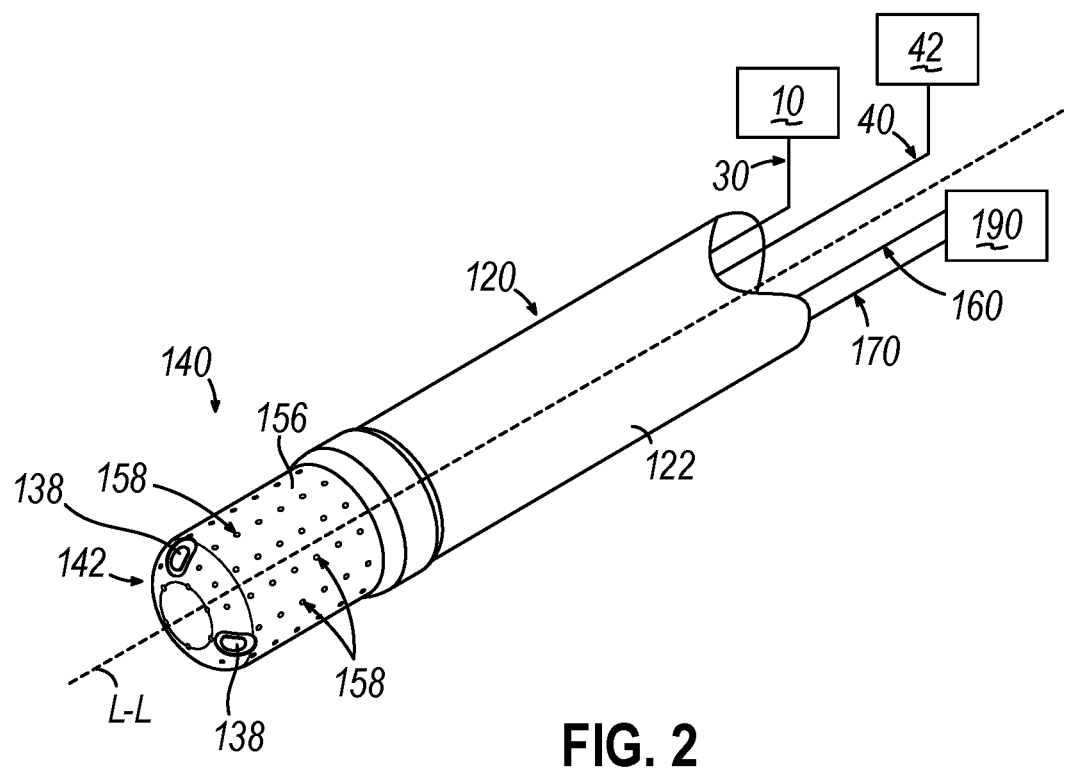
FIG. 2 depicts a perspective view of a distal portion of the catheter of FIG. 1, with additional components shown in schematic form.

As shown in FIG. 2, catheter (120) includes an elongate flexible sheath (122), with end effector (140) being disposed at a distal end of sheath (122). End effector (140) and various components that are contained in sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly (150) in end effector (140). In such versions, the processor of console (12) is also operable to process the position indicative signals from navigation sensor assembly (150) to thereby determine the position of end effector (140) within the patient (PA). As will be described in greater detail below, navigation sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a navigation sensor assembly (150).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from navigation sensor assembly (150) of end effector (140). For instance, as end effector (140) of catheter (120) moves within the patient (PA), the corresponding position data from navigation sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). The processor of console (12) may also drive display (18) to superimpose the current location of end effector (140) on the images of the patient's anatomy, such as by superimposing an illuminated dot, a crosshair, a graphical representation of end effector (140), or some other form of visual indication.

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. Exemplary End Effector of Catheter Assembly

Figure 3:
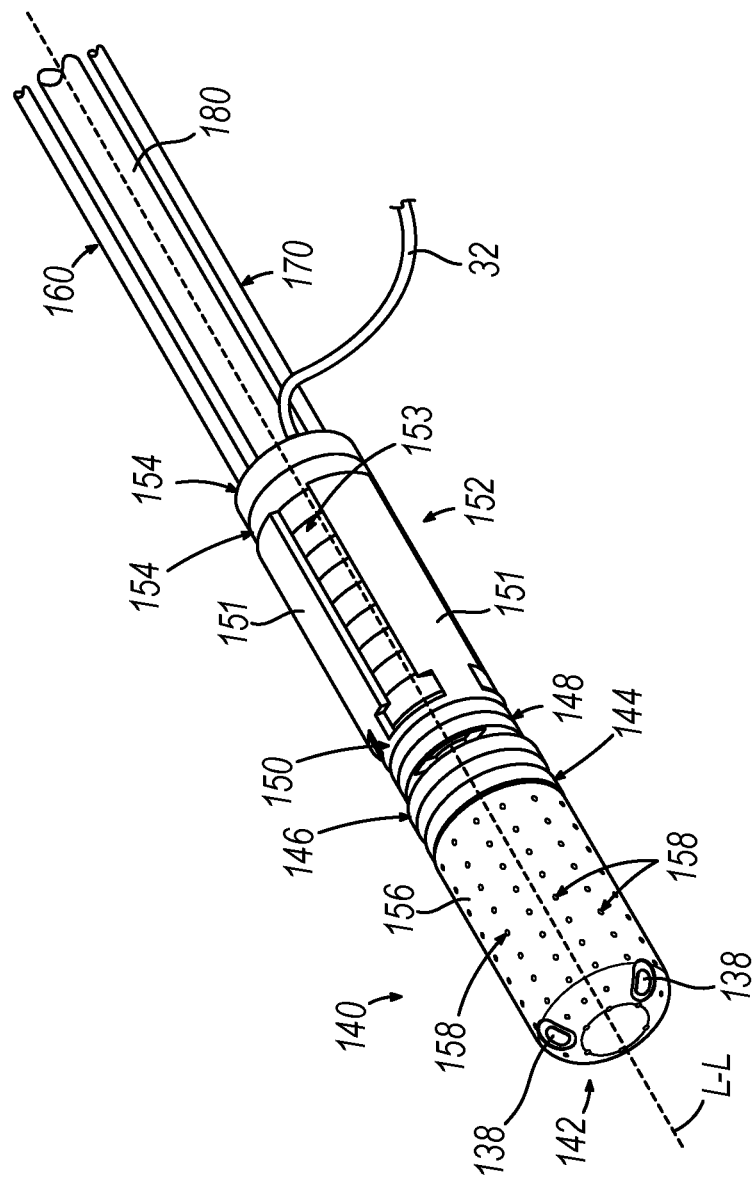
FIG. 3 depicts a perspective view of the distal portion of the catheter of FIG. 1, with an outer sheath omitted to reveal internal components.
Figure 4:
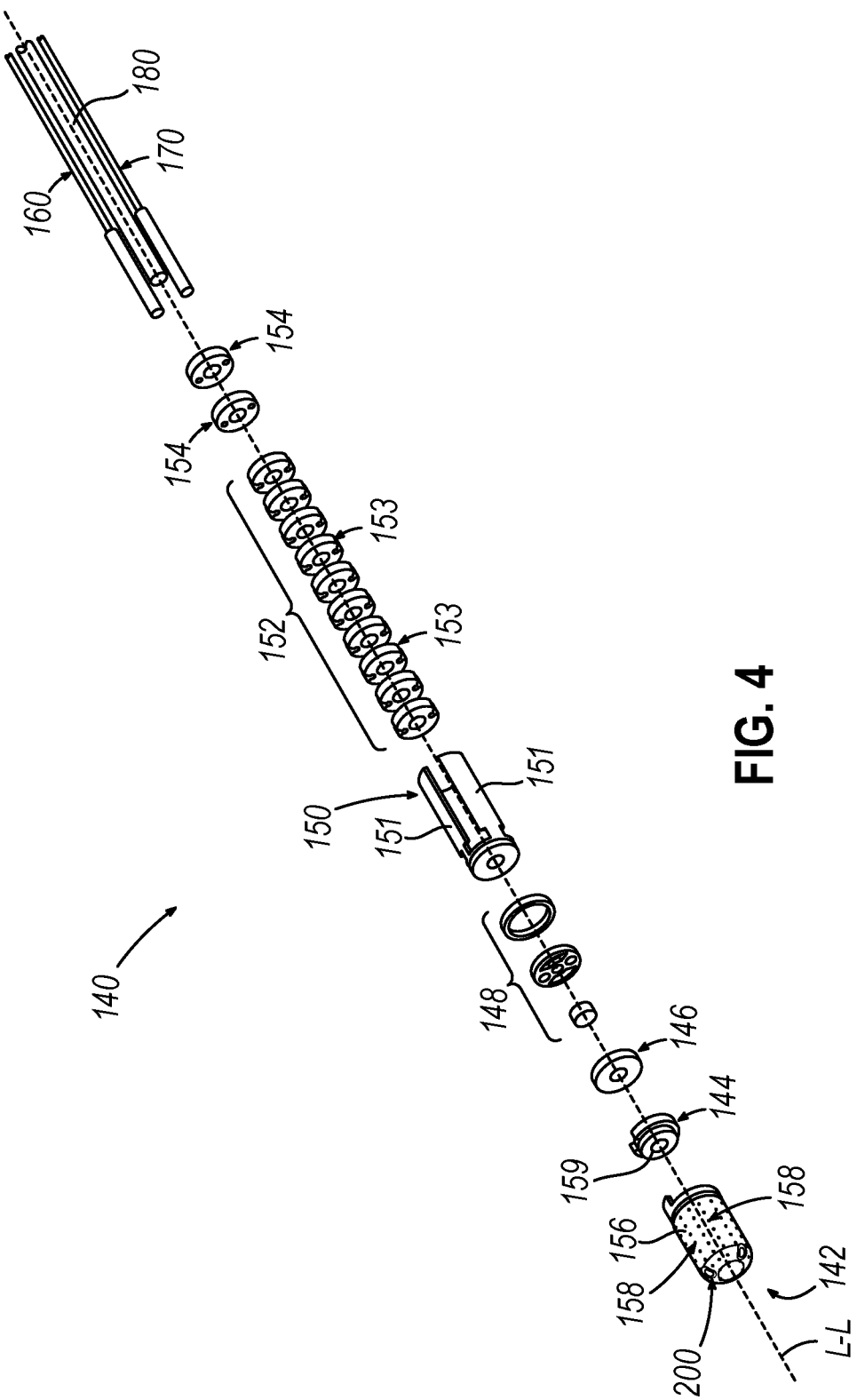
FIG. 4 depicts an exploded perspective view of the distal portion of the catheter of FIG. 1.

FIGS. 2-4 show exemplary components of end effector (140), and other components of the distal portion of catheter (120), in greater detail. End effector (140) includes a distal tip member (142), a distal tip base (144), a distal circuit disk (146), a strain gauge assembly (148), a navigation sensor assembly (150), a distal spacer stack (152) of distal spacers (153), and a pair of proximal spacers (154). Distal tip member (142), distal tip base (144), distal circuit disk (146), strain gauge assembly (148), navigation sensor assembly (150), distal spacer stack (152), and proximal spacers (154) are coaxially aligned with each other and are stacked longitudinally so that these components (144-154) define a stacked circuit. A pair of push-pull cables (160, 170) and an irrigation tube (180) extend along the length of catheter (120) to reach end effector (140). Each of the foregoing components will be described in greater detail below. Flexible sheath (122) surrounds all of the foregoing components except for distal tip member (142).

As shown in FIGS. 3-4, distal tip member (142) of the present example is electrically conductive and includes a cylindraceous body (156) with a dome tip. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximal-most spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). First driver module (14) may process the EP mapping signals and provide the physician (PH) with corresponding feedback indicating the locations of aberrant electrical activity in accordance with the teachings of various references cited herein. EP mapping microelectrodes (138) and related components will be described in further detail below.

Strain gauge assembly (148) is positioned proximal to distal circuit disk (146) and is configured to sense external forces that impinge against distal tip member (142). When distal tip member (142) encounters external forces (e.g., when distal tip member (142) is pressed against tissue), those external forces are communicated from distal tip member (142) to distal tip base (144), to distal circuit disk (146), and to strain gauge assembly (148) such that strain gauge may generate a suitable signal corresponding to the magnitude and direction of the external force.

Navigation sensor assembly (150) may generate signals indicating the position and orientation of end effector (140) in three-dimensional space with substantial precision. The signals from navigation sensor assembly (150) may be communicated via other structures in the layers that are proximal to strain navigation sensor assembly (150), eventually reaching first driver module (14) of console (12) via cable (30).

As noted above and as shown in FIGS. 1-2, cable (30) couples catheter assembly (100) with drive system (10). As shown in FIG. 3, wires (32) of cable (30) extend along the length of catheter (120) to reach the proximal-most proximal spacer (154).

As also noted above, catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 3-4. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through a central passageway formed by aligned central apertures of the features described above, ultimately reaching an interior (157) of distal tip member (142) via aperture (159) of distal tip base (144) prior to flowing out from openings (158).

As noted above, and as shown in FIGS. 2-4, catheter (100) of the present example further includes a pair of push-pull cables (160, 170). Push-pull cables (160, 170) enable the physician (PH) to selectively deflect end effector (140) laterally away from a longitudinal axis (L-L), thereby enabling the physician (PH) to actively steer end effector (140) within the patient (PA). Various mechanisms that may be used to drive push-pull cables (160, 170) in a simultaneous, longitudinally-opposing fashion will be apparent to those skilled in the art in view of the teachings herein.

III. Exemplary Insert-Molded Microelectrode

Figure 5:
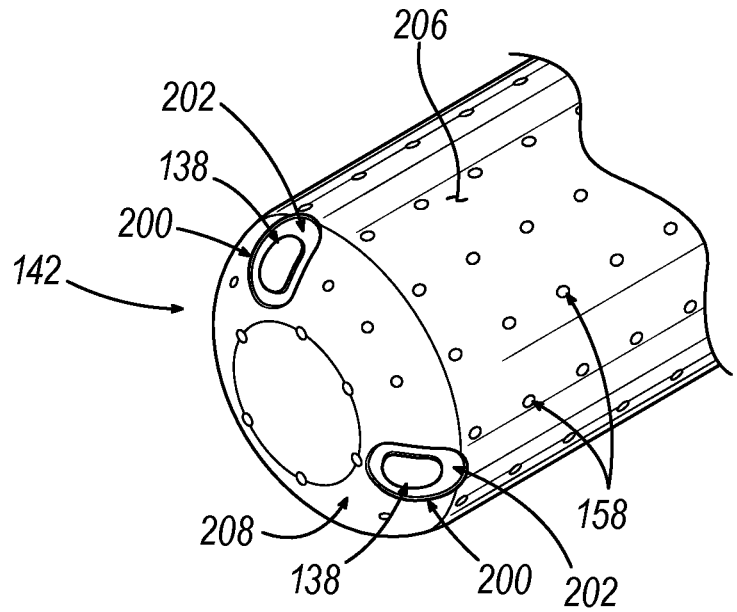
FIG. 5 depicts an enlarged partial perspective view of the distal tip portion of the catheter of FIG. 1, showing an insert-molded microelectrode.
Figure 6:
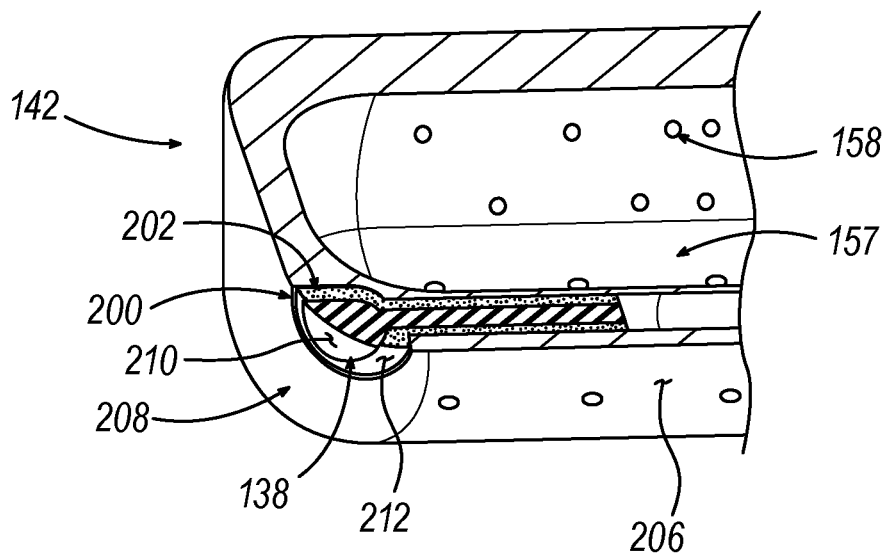
FIG. 6 depicts a perspective view in cross section of the distal tip portion of the catheter of FIG. 5.
Figure 7:
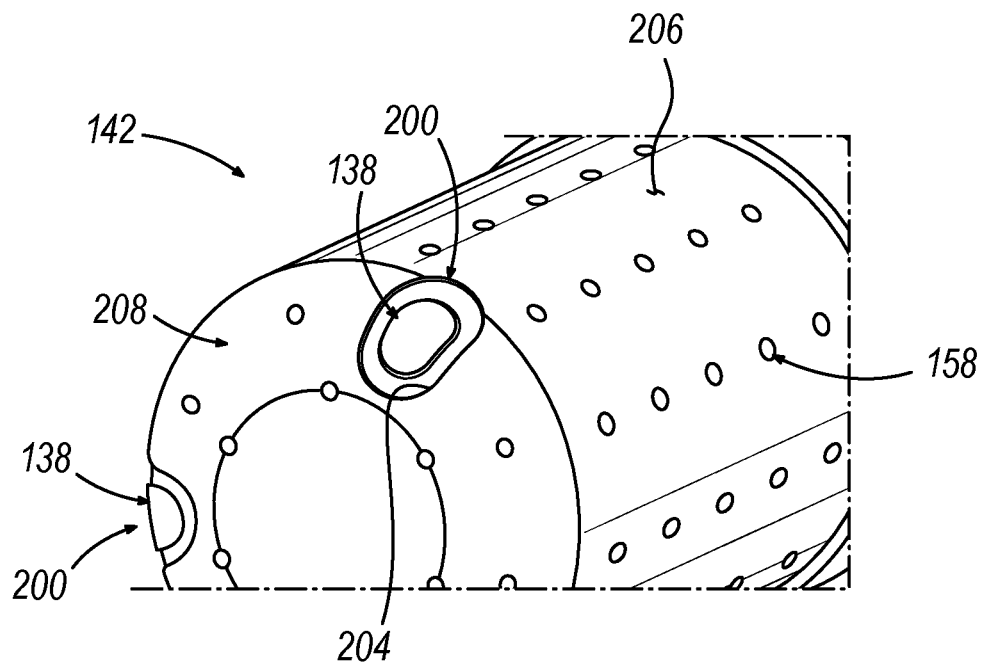
FIG. 7 depicts a perspective view of the distal portion of the catheter of FIG. 1, shown with a composite of the insert in phantom.

FIGS. 5-7 illustrate insert-molded microelectrodes (200), which may also be referred to herein as inserts (200). Each insert-molded microelectrode or insert (200) includes microelectrode (138) and a composite (202). Microelectrodes (138) are constructed of a platinum-iridium material in the present example, however, other suitable materials may be used instead or as well. Composite (202) is a non-conductive material in the present example, which electrically isolates microelectrodes (138) from cylindraceous body (156) of tip member (142) of end effector (140). By way of example only, composite (202) may be formed of polycarbonate, PEEK (polyether etherketone), polyethylene, UHMWPE (ultra high weight molecular polyethylene), or ABS. Alternatively, composite (202) may be formed of any other suitable material(s) such as Ultem (polyetherimide), polysulfone or a hard elastomeric compound such as 65D Pebax.

Insert-molded microelectrodes (200) are located in tip member (142) of end effector (140). Inserts (200) extend longitudinally and parallel with longitudinal axis L-L in the present example, but in other examples inserts (200) can have other orientations with respect to longitudinal axis L-L. To accommodate insert-molded microelectrodes (200), tip member (142) includes bores (204). Tip member (142) also includes a shell (206) defining an outer surface of tip member (142). Bores (204) extend longitudinally from and through shell (206) proximally toward handle (110) of catheter assembly (100), and each bore (204) is configured to receive one insert-molded microelectrode (200). In the present example, end effector (140) is configured with three insert-molded microelectrodes (200); however, in other versions, end effector (140) can be configured with greater or fewer insert-molded microelectrodes (200).

As mentioned above, tip member (142) includes cylindraceous body (156) such that an outer surface of shell (206) defines a contour. Insert-molded microelectrodes (200) are shaped to conform to this contour of the outer surface of shell (206) when insert-molded microelectrodes are positioned within bores (204). In this manner, conforming to the contour of the outer surface of shell (206) can be understood to mean that a distal surface of inserts (200) follows or is flush with an adjacent distal surface of shell (206). In the illustrated version of a conforming configuration, the outer surface of shell (206) includes a curved region (208) that extends circumferentially around tip member (142). Bore (204) is positioned in curved region (208) with the distal end of bore (204) located in curved region (208). Insert (200) is further positionable in bore (204) within curved region (208) with the distal surface of insert (200) located in curved region (208). In this example, curved region (208), outer surface of shell (206), distal surface of microelectrode (138), and distal surface of composite (202) have a curved parallel arrangement where the surfaces of each are curved and parallel to one another.

Still referring to the example of FIGS. 5-7, microelectrode (138) of insert (200) has a distal surface (210) that protrudes distally from a distal surface (212) of composite (202) of insert (200). With this configuration, distal surface (210) of microelectrode (138) is curved and extends parallel with the contour of the outer surface of shell (206). Similarly, distal surface (212) of composite (202) is also curved and extends parallel with the contour of the outer surface of shell (206). In this exemplary arrangement, distal surface (212) of composite (202) is recessed relative to the outer surface of shell (206), while distal surface (210) of microelectrode (138) is flush with the outer surface of shell (206). Also, as best seen in FIG. 6, in the present example within tip member (142), microelectrode (138) of insert (200) extends further proximally relative to composite (202) of insert (200). However, in other versions composite (202) may extend further or shorter within tip member (142) relative to microelectrode (138) than the configuration illustrated in FIG. 6.

Figure 8A:
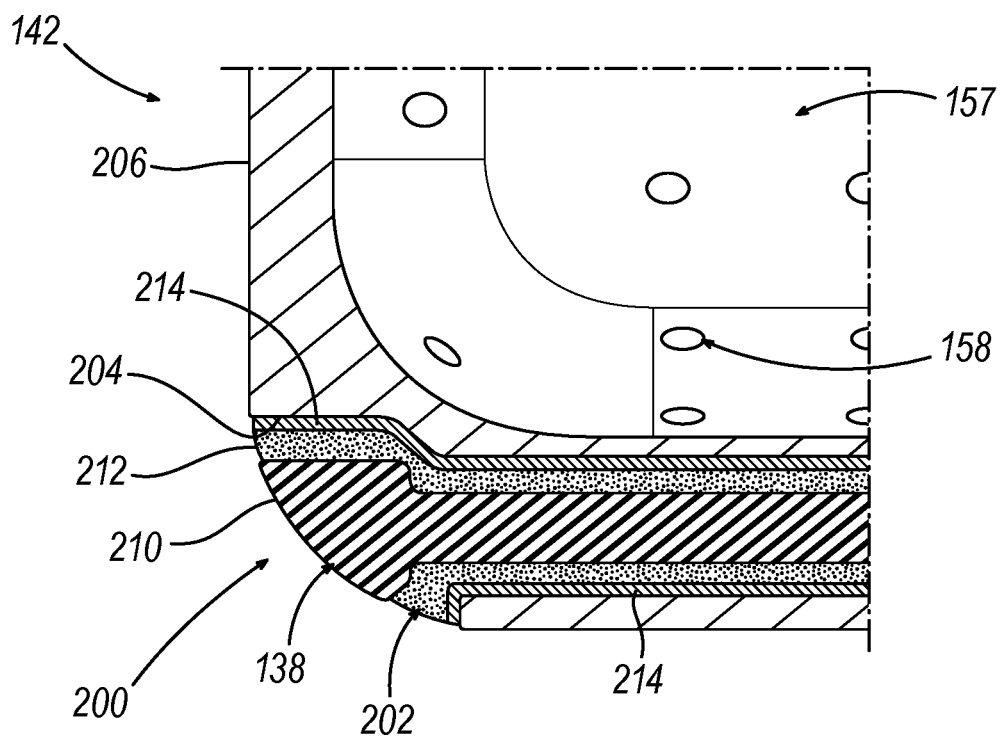
FIG. 8A depicts an enlarged partial side view in cross section of the distal portion of the catheter of FIG. 5.

FIG. 8A illustrates a cross section of a portion of a distal end of tip member (142) of end effector (140). In the present example, an adhesive (214) is used for secure connection of insert-molded microelectrode (200) to bore (204) of tip member (142). As shown in the example of FIG. 8A, adhesive (214) is located along an interior wall of tip member (142) that defines bore (204) and further contacts an outer wall of composite (202). In this manner, adhesive (214) is located between insert-molded microelectrode (200) and tip member (142) to thereby attach these components together. While the present example shows adhesive (214) extending along all of the depicted length of bore (204) and insert (200), in other versions the adhesive (214) is applied to less than this length. A suitable adhesive application in this respect will securely retain insert-molded microelectrode (200) within bore (204) of tip member (142).

In some other versions, adhesive (214) is omitted entirely. For instance, in one such other version without adhesive (214), insert-molded microelectrode (200) has an interference fit with bore (204) of tip member (142). In this manner, the respective sizes of bore (204) and insert (200) are such that there is engaging contact between the inner surface of tip member (142) defining bore (204) and the outer surface of insert (200) when insert (200) is positioned within bore (204). Furthermore, in this arrangement, there is sufficient frictional force between bore (204) of tip member (142) and insert (200) to securely retain inserts (200) within bore (204) of tip member (142) without adhesive or other features.

Figure 8B:
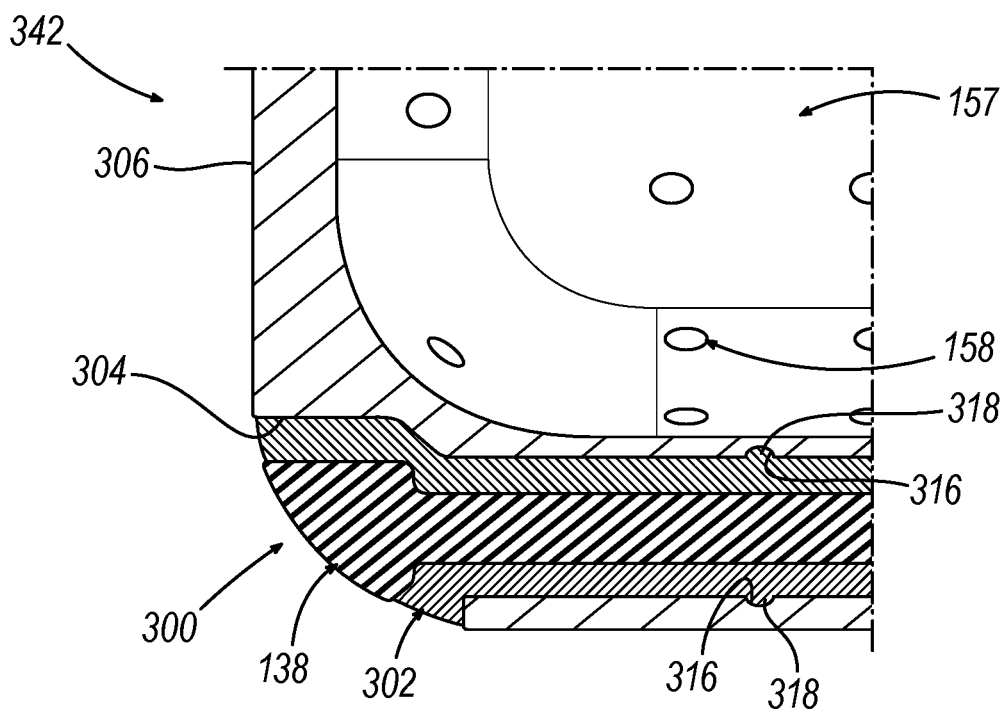
FIG. 8B depicts an enlarged partial side view in cross section of another exemplary distal portion of a catheter that can be used in place of the catheter of FIG. 5.
Figure 9A:
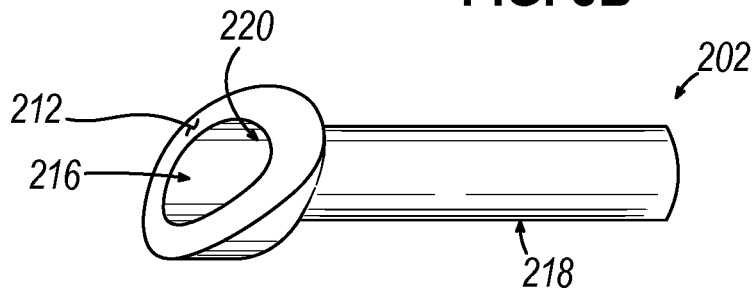
FIG. 9A depicts a perspective view of the composite of the insert-molded microelectrode.
Figure 9B:
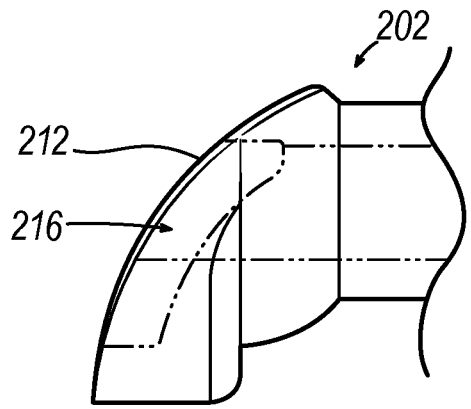
FIG. 9B depicts a partial side view of the composite of the insert-molded microelectrode of FIG. 9A.
Figure 9C:
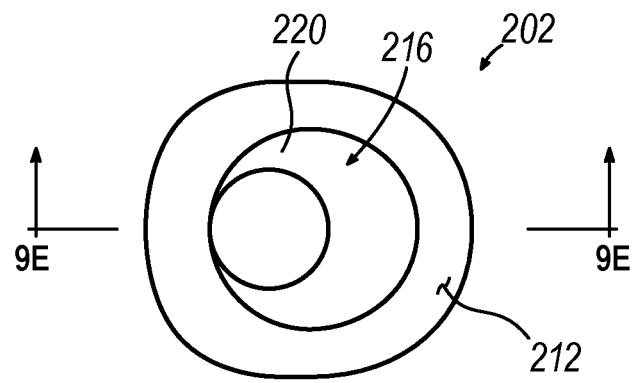
FIG. 9C depicts a top view of the composite of the insert-molded microelectrode of FIG. 9A.
Figure 9D:
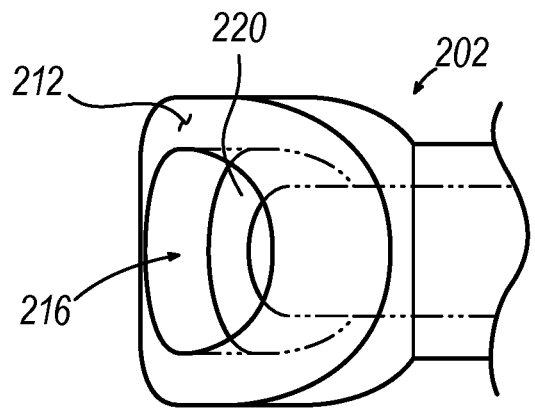
FIG. 9D depicts a front view of the composite of the insert-molded microelectrode of FIG. 9A.
Figure 9E:
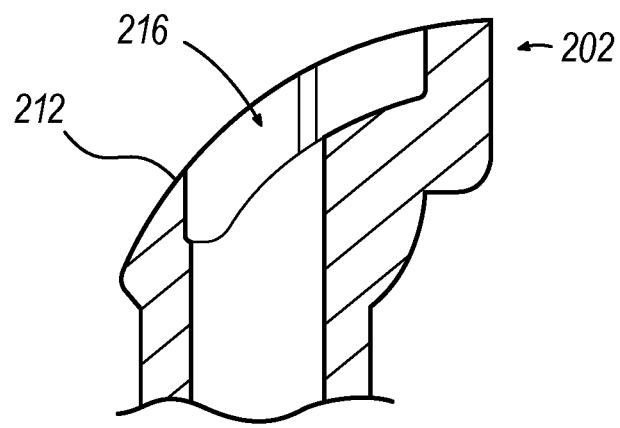
FIG. 9E depicts a side view in cross section of the composite of the insert-molded microelectrode of FIG. 9A taken along line 9E-9E of FIG. 9C.

In another exemplary version, where insert-molded microelectrodes can be used with or without adhesive for attachment with a tip member of a catheter end effector, a pair of engaging features are used. For instance, FIG. 8B illustrates a cross section of a distal end of another exemplary tip member (342) that can be used instead of tip member (142) with end effector (140). Tip member (342) includes a shell (306) having a bore (304) configured to receive an insert-molded microelectrode (300). Bore (304) is configured with one or more engaging features (316). Furthermore, composite (302) of insert (300) is configured with one or more engaging features (318). Engaging features (316) are configured to engage with or connect with engaging features (318) to thereby connect or attach insert-molded microelectrode (300) with tip member (342). In the present example, this connection between insert-molded microelectrode (300) and tip member (342) is configured as a permanent connection. However, in other versions this connection may be selective such that insert (300) can be removed from tip member (342) either with or without the use of special tools to accomplish such removal. In either case however, the connection between insert (300) and tip member (342) is configured to be stable during use such that insert (300) remains securely within bore (304).

In the present example of FIG. 8B, engaging features (316) of bore (304) are configured as semi-spherical recesses or cut-outs. Meanwhile, engaging features (318) of composite (302) are configured as semi-spherical protrusions. In this manner, engaging features (316) and engaging features (318) are complementary such that engaging features (316) are configured to receive engaging features (318) and in doing so define an interference or snap fit that secures insert-molded microelectrode (300) to and with tip member (342). In the present example, engaging features (318) of insert (300) are resilient features such that engaging feature (318) may compress slightly when inserting insert-molded microelectrode (300) into bore (304) and then expand once engaging feature (318) is seated or located within engaging feature (316). In this way, insert (300) includes a resilient feature configured to engage with an interior wall of bore (304). In other versions, engaging features (316) and engaging features (318) have forms and shapes different than the semi-spherical recesses and protrusions shown in FIG. 8A.

FIGS. 9A-9E depict composite (202) or portions thereof. Composite (302) mentioned above would have the same construction and configuration except for the addition of engaging features (318) with composite (302). As shown in FIGS. 9A-9E, composite (202) includes an opening (216) where microelectrode (138) resides after insert molding. Composite (202) also has a proximally extending cylindrical portion (218) where a proximal portion of microelectrode (138) resides after insert molding. As shown in the present example, opening (216) within cylindrical portion (218) has a smaller diameter than the diameter of opening (216) at the distal end of composite (202). After insert molding with microelectrode (138), composite (202) defines a flange (220) around the region of opening (216) where the smaller diameter begins. With this configuration, microelectrode (138) seats against flange (220) after insert molding. As mentioned above, distal surface (212) of composite (202) has a curved shaped in the present example such that distal surface (212) is parallel with curved region (208) of tip member (142). Composite (202) is constructed of a non-conductive material and is configured so that microelectrode (138) is isolated from contact with tip member (142) as mentioned above. While the present example describes composite (202) as being formed during an insert-molded process using microelectrode (138), in some other versions, composite (202) can be formed separate from microelectrode (138) and thereafter joined or combined with microelectrode (138).

IV. Exemplary Method of Attaching a Microelectrode to an End Effector

Figure 10:
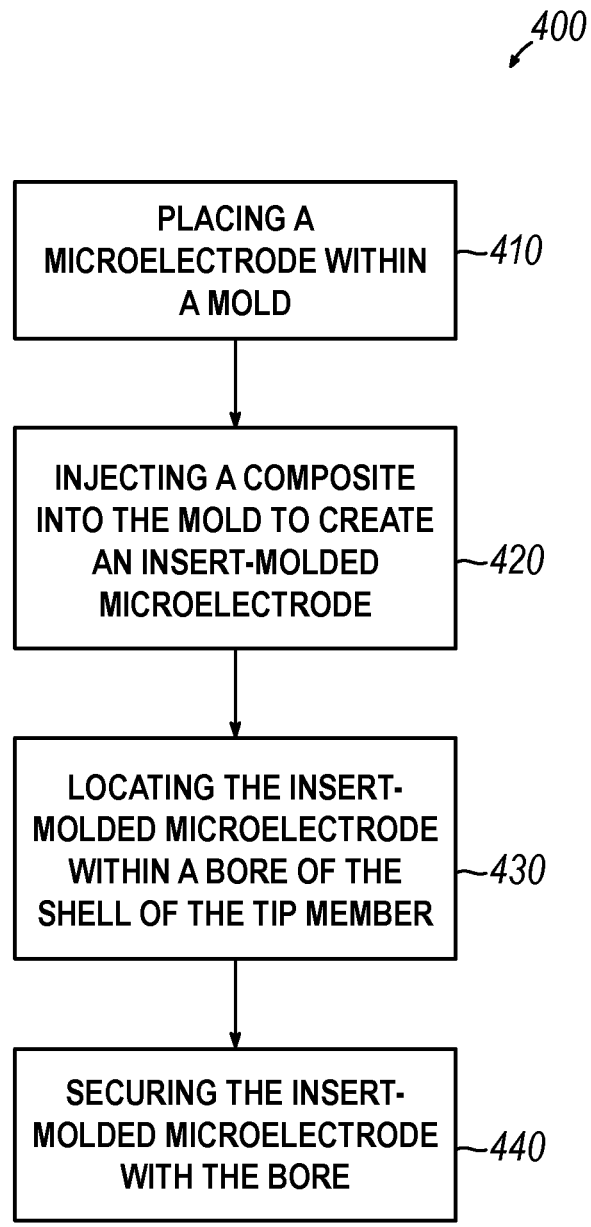
FIG. 10 depicts a schematic view of a method of attaching the insert-molded microelectrode with the distal end of the catheter of FIG. 1.

FIG. 10 depicts an exemplary method (400) usable to make an insert-molded microelectrode and attach the insert-molded microelectrode to an end effector of a catheter such as end effector (140) of catheter (120). With method (400) begins with step (410) that includes placing a microelectrode (138) within a mold. Thereafter, step (420) includes injecting composite (202, 302) into the mold to create insert-molded microelectrode (200, 300). With insert-molded microelectrode (200, 300) formed, step (430) includes locating insert-molded microelectrode (200, 300) within bore (204, 304) of shell (206, 206) of tip member (142, 342). Finally, step (440) includes securing insert-molded microelectrode (200, 300) within bore (204, 304). This securing step can be achieved in various ways as described above and may include an adhesive application prior to step (430). Of course, as mentioned above, some versions without adhesive may instead incorporate engaging features (316, 318) with tip member (342) and composite (302) when fabricating these components. In view of the teachings herein, other actions within these steps or other steps that may be used as well or omitted will be apparent to those skilled in the art.

V. Exemplary System for Insert-Molded Microelectrodes

Figure 11:
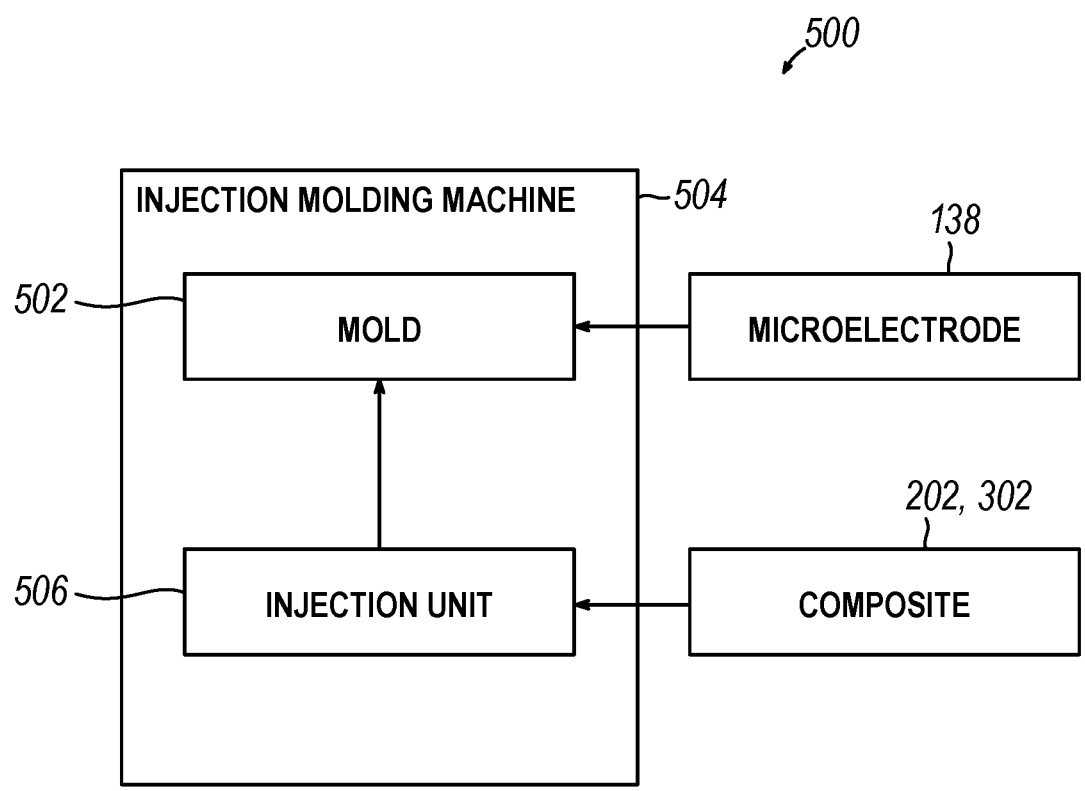
FIG. 11 depicts a schematic view of an insert-molding system for use in making the insert-molded microelectrode of FIG. 5.

FIG. 11 depicts an exemplary system (500) usable with making an insert-molded microelectrode such as insert-molded microelectrodes (200, 300) described above. In system (500) of this example, microelectrode (138) is positionable within a mold (502) of an injection molding machine (504). With microelectrode (138) within mold (502), and with mold (502) positioned within injection molding machine (504), composite (202, 302) is added to an injection unit (506) of injection molding machine (504). Injection unit (506) directs composite (202, 302) into mold (502) where composite (202, 302) combines with microelectrode (138) to thereby form insert-molded microelectrode (200, 300). After forming and cooling such that composite (202, 302) is solid, mold (502) can be opened and insert-molded microelectrode (200, 300) removed from mold (502). Finishing processes can be conducted with insert-molded microelectrode (200, 300) as needed or desired. With insert-molded microelectrode fabricated, method (400) can be continued from step (430) to connect or attach insert-molded microelectrode (200, 300) with tip member (142, 342) of end effector (140) of catheter (120) as described above. It should be noted that system (500) is merely exemplary, and other systems for fabricating insert-molded microelectrodes (200, 300) can be used and will be apparent to those skilled in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for use in a medical procedure to conduct electrophysiological mapping comprises a body and an end effector connected with a distal end of the body. The end effector includes a tip member at the distal end of the end effector. The tip member has a shell that defines an outer surface of the tip member. The tip member further has a bore located in the outer surface of the shell. The end effector also includes an insert positionable within the bore of the tip member. The insert includes a microelectrode and a non-conductive composite configured to act as a contact barrier between the microelectrode and the shell. The insert is shaped to conform to a contour of the outer surface of the shell.

Example 2

The apparatus of Example 1, the bore of the tip member extending longitudinally in a proximal direction toward the body.

Example 3

The apparatus of any one or more of Example 1 through Example 2, the microelectrode made from platinum-iridium.

Example 4

The apparatus of any one or more of Example 1 through Example 3, further comprising an adhesive configured to adhere the composite to the shell.

Example 5

The apparatus of any one or more of Example 1 through Example 3, the insert further includes an engaging feature configured to engage with an interior wall of the bore.

Example 6

The apparatus of Example 5, the engaging feature being resilient and making a snap-fit connection with the bore.

Example 7

The apparatus of any one or more of Example 5 through Example 6, the engaging feature being configured to engage with the bore to make a permanent connection between the insert and the shell.

Example 8

The apparatus of any one or more of Example 1 through Example 3 and Example 5 through Example 7, the insert being configured to connect with the shell without the use of adhesive.

Example 9

The apparatus of any one or more of Example 1 through Example 8, the microelectrode being insert-molded with the composite to form the insert.

Example 10

The apparatus of any one or more of Example 1 through Example 9, the tip member having a plurality of openings configured to deliver an irrigation fluid.

Example 11

The apparatus of any one or more of Example 1 through Example 10, the tip member being configured to deliver electrical energy to a target site.

Example 12

The apparatus of any one or more of Example 1 through Example 11, the body defining a longitudinal axis, with the end effector being configured to deflect away from the longitudinal axis.

Example 13

The apparatus of Example 12, further comprising a push-pull cable configured to guide the end effector and operable to deflect the end effector away from the longitudinal axis.

Example 14

The apparatus of Example 12, further comprising a pair of push-pull cables configured to guide the end effector and operable to deflect the end effector away from the longitudinal axis.

Example 15

The apparatus of any one or more of Example 1 through Example 14, the outer surface of the shell including a curved region that extends circumferentially around the tip member, the bore being positioned in the curved region, and the insert being positionable in the bore within the curved region.

Example 16

The apparatus of any one or more of Example 1 through Example 15, the apparatus having multiple bores in the outer surface of the shell with multiple inserts, each bore being configured to receive one of the inserts.

Example 17

The apparatus of Example 16, having a plurality of inserts configured as insert-molded microelectrodes.

Example 18

The apparatus of any one or more of Example 1 through Example 17, the microelectrode of the insert having a distal surface that protrudes distally from a distal surface of the composite of the insert.

Example 19

The apparatus Example 18, the distal surface of the microelectrode being curved and extending parallel with the contour of the outer surface of the shell.

Example 20

The apparatus of any one or more of Example 18 through Example 19, the distal surface of the composite being curved and extending parallel with the contour of outer surface of the shell.

Example 21

The apparatus of any one or more of Example 18 through Example 20, the distal surface of the composite being recessed relative to the outer surface of the shell.

Example 22

The apparatus of any one or more of Example 18 through Example 21, the distal surface of the microelectrode extending flush with the outer surface of the shell.

Example 23

The apparatus of any one or more of Example 1 through Example 22, the microelectrode of the insert extending further proximally relative to the composite of the insert.

Example 24

A method for attaching a microelectrode with a medical instrument used for electrophysiological mapping comprises (a) placing a microelectrode within a mold; (b) injecting a composite into the mold to create an insert-molded microelectrode formed of the microelectrode and the composite, the insert-molded microelectrode having an outer surface that conforms to an outer surface of a shell of a tip member of an end effector of the medical instrument; (c) locating the insert-molded microelectrode within a bore of the shell of the tip member, the bore configured to receive the insert-molded microelectrode; and (d) securing the insert-molded microelectrode within the bore.

Example 25

The method of Example 24, further comprising applying an adhesive to a select one or both of an interior of the bore and an outer surface of the composite prior to locating the inset-molded electrode within the bore.

Example 26

The method of Example 24, the composite having a molded engaging feature configured to attach with a complementary engaging feature of the bore for securing the insert-molded microelectrode within the bore.

Example 27

The method of any one or more of Example 24 through Example 26, the locating and the securing steps occurring substantially contemporaneously.

Example 28

The method of Example 24 accomplished using the apparatus of any one or more of Example 1 through Example 23.

VII. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for use in a medical procedure to conduct electrophysiological mapping, the apparatus comprising:
    (a) a body; and
    (b) an end effector connected with a distal end of the body, the end effector including:
       (i) a tip member at the distal end of an end effector, the tip member having a first longitudinal axis and a shell that defines an outer surface of the tip member, the tip member further having an elongated bore located in the outer surface of the shell and parallel with the first longitudinal axis, and (ii) an insert positionable within the elongated bore of the tip member, the insert including a microelectrode and a non-conductive molded composite configured to act as a contact barrier between the microelectrode and the shell, the insert shaped to conform to a contour of the outer surface of the shell,
    (1) the microelectrode including:
        (A) a microelectrode distal surface,
        (B) a microelectrode distal portion comprising a first outer circumference, and
        (C) an elongated microelectrode proximal portion comprising a second outer circumference, wherein the second outer circumference is smaller than the first outer circumference,
    (2) the non-conductive molded composite including:
        (A) a composite distal portion circumferentially surrounding the microelectrode distal portion,
        (B) a composite distal surface surrounding the microelectrode distal surface,
        (C) an elongated composite proximal portion surrounding the elongated microelectrode proximal portion, and
        (D) a flange formed by an inner surface of the composite distal portion and the elongated composite proximal portion, the microelectrode distal portion being seated in the flange.

2. The apparatus of claim 1, the elongated bore of the tip member extending longitudinally in a proximal direction toward the body.

3. The apparatus of claim 1, the insert further including an engaging feature configured in the elongated composite proximal portion configured to engage with an interior wall of the elongated bore.

4. The apparatus of claim 3, the engaging feature being resilient and making a snap-fit connection with the elongated bore.

5. The apparatus of claim 3, the engaging feature being configured to engage with the elongated bore to make a permanent connection between the insert and the shell.

6. The apparatus of claim 1, the insert being configured to connect with the shell without the use of adhesive.

7. The apparatus of claim 1, the tip member having a plurality of openings configured to deliver an irrigation fluid.

8. The apparatus of claim 1, the tip member being configured to deliver electrical energy to a target site.

9. The apparatus of claim 1, the body defining a second longitudinal axis, with the end effector being configured to deflect away from the second longitudinal axis.

10. The apparatus of claim 1, the outer surface of the shell including a curved region that extends circumferentially around the tip member, the elongated bore being positioned in the curved region, and the insert being positionable in the elongated bore within the curved region.

11. The apparatus of claim 1, the apparatus having multiple elongated bores in the outer surface of the shell with multiple inserts, each of the multiple elongated bores being configured to receive one of the inserts.

12. The apparatus of claim 1, the microelectrode distal surface protrudes distally from the non-conductive molded composite distal surface.

13. The apparatus of claim 12, the microelectrode distal surface being curved and extending parallel with the contour of the outer surface of the shell.

14. The apparatus of claim 12, the non-conductive molded composite distal surface being curved and extending parallel with the contour of outer surface of the shell.

15. The apparatus of claim 12, the non-conductive molded composite distal surface being recessed relative to the outer surface of the shell.

16. The apparatus of claim 12, the microelectrode distal surface of the microelectrode extending flush with the outer surface of the shell.

17. The apparatus of claim 1, the microelectrode of the insert extending further proximally relative to the non-conductive molded composite of the insert.

\* \* \* \* \*